(12) United States Patent
Paul

(10) Patent No.: US 11,039,936 B2
(45) Date of Patent: Jun. 22, 2021

(54) MEDICAL IMPLANT EXTRACTION DEVICE

(71) Applicant: RP Medical Inc., Maple Ridge (CA)

(72) Inventor: Ross Edward Paul, Maple Ridge (CA)

(73) Assignee: RP Medical Inc., Maple Ridge (CA)

( * ) Notice: Subject to any disclaimer, the term of this patent is extended or adjusted under 35 U.S.C. 154(b) by 0 days.

(21) Appl. No.: 15/347,518

(22) Filed: Nov. 9, 2016

(65) Prior Publication Data

US 2017/0119547 A1 May 4, 2017

Related U.S. Application Data

(63) Continuation of application No. 13/080,620, filed on Apr. 5, 2011, now abandoned.

(Continued)

(51) Int. Cl.
*A61F 2/46* (2006.01)
*A61B 17/3211* (2006.01)
*A61C 3/00* (2006.01)

(52) U.S. Cl.
CPC ........... *A61F 2/461* (2013.01); *A61B 17/3211* (2013.01); *A61C 3/00* (2013.01); *A61F 2/4603* (2013.01);

(Continued)

(58) Field of Classification Search
CPC ...... A61F 2002/4603; A61F 2002/4681; A61F 2002/4619; A61F 2002/461; A61F 2/46; A61F 2/4603; A61F 2/461; A61F 2/4609; A61F 2/4612; A61F 2/4614; A61F 2/4619; A61F 2002/4631; A61B 17/3211; A61B 17/1668; A61B 17/1659; A61B 17/076; A61B 17/16; A61B 17/1604; A61B 17/32; A61B 17/320004; A61B 17/320008; A61B 17/56; A61B 17/88; A61B 17/92; A61C 3/00

(Continued)

(56) References Cited

U.S. PATENT DOCUMENTS 1,890,273 A 12/1932 Wells
2,121,193 A 6/1938 Hanicke (Continued)

FOREIGN PATENT DOCUMENTS

CA 2013746 10/1999
CN 2415730 1/2001

(Continued)

OTHER PUBLICATIONS

International Search Report issued by the Canadian Intellectual Property Office in connection with International Patent Application No. PCT/CA2011/000404, dated Jul. 8, 2011, 5 pages.

(Continued)

*Primary Examiner* — Marcela I. Shirsat

(57) ABSTRACT

Extraction instruments and systems for use in revision arthroplasty are provided. The extraction instruments are shaped and configured to fit within the typically tight confines in which revision arthroplasty is performed, and to enhance the surgeon's control over the axis, quantum and speed of the force that is required be applied to disrupt a bone-to-prosthesis bond. This enables completion of a revision arthroplasty to proceed more quickly, and with reduced risk that unwanted movements might cause accidental injury to nearby vital structures.

11 Claims, 9 Drawing Sheets

Related U.S. Application Data

(60) Provisional application No. 61/341,785, filed on Apr. 5, 2010.

(52) U.S. Cl.
CPC .............. *A61F 2002/4619* (2013.01); *A61F 2002/4681* (2013.01)

(58) Field of Classification Search
USPC ... 606/99, 100, 104, 86 A, 86 B, 53, 79, 84, 606/86 R, 88, 90, 91, 105, 167; 623/22.12; 30/314; 254/25, 21
See application file for complete search history.

(56) References Cited

U.S. PATENT DOCUMENTS

| | | | |
|---|---|---|---|
| 3,212,187 A | 10/1965 | Benedict | |
| 3,367,335 A | 2/1968 | Ward et al. | |
| 4,153,053 A * | 5/1979 | Figallo | A61B 17/8866 606/100 |
| 4,290,583 A | 9/1981 | Lombardi | |
| 4,459,985 A | 7/1984 | McKay et al. | |
| 4,688,570 A * | 8/1987 | Kramer | A61F 9/013 606/166 |
| 4,885,004 A * | 12/1989 | Pao | A61B 17/3211 604/22 |
| 4,944,760 A | 7/1990 | Kenna | |
| 5,013,314 A | 5/1991 | Firica et al. | |
| 5,085,663 A * | 2/1992 | Tarr | A61B 17/3211 30/294 |
| 5,203,865 A * | 4/1993 | Siepser | A61B 17/3211 30/162 |
| 5,217,477 A * | 6/1993 | Lager | A61B 17/3211 30/355 |
| 5,323,765 A | 6/1994 | Brown | |
| 5,423,842 A | 6/1995 | Michelson | |
| 5,702,463 A | 12/1997 | Pothier et al. | |
| 5,934,905 A * | 8/1999 | Martoral | A61C 3/00 30/342 |
| 6,565,575 B2 | 5/2003 | Lewis | |
| 7,131,982 B1 | 11/2006 | Karapetyan | |
| 7,185,879 B1 | 3/2007 | Lejuez | |
| 7,998,146 B2 | 8/2011 | Anderson | |
| 2002/0116007 A1* | 8/2002 | Lewis | A61B 17/1666 606/99 |
| 2003/0100905 A1 | 5/2003 | Mears | |
| 2006/0089656 A1 | 4/2006 | Allard et al. | |
| 2006/0242843 A1 | 11/2006 | Schoenberg | |
| 2013/0046313 A1* | 2/2013 | Lian | A61B 17/92 606/99 |

FOREIGN PATENT DOCUMENTS

| | | |
|---|---|---|
| WO | 8702572 A1 | 5/1987 |
| WO | 9310704 A1 | 6/1993 |
| WO | 2007098549 A1 | 9/2007 |

OTHER PUBLICATIONS

Written Opinion of the International Searching Authority issued by the Canadian Intellectual Property Office in connection with International Patent Application No. PCT/CA2011/000404, dated Jul. 8, 2011, 6 pages.

European Patent Office, Extended European Search Report, in connection with related European Patent Application No. 11764996.2, dated Aug. 23, 2016, 12 pages.

* cited by examiner

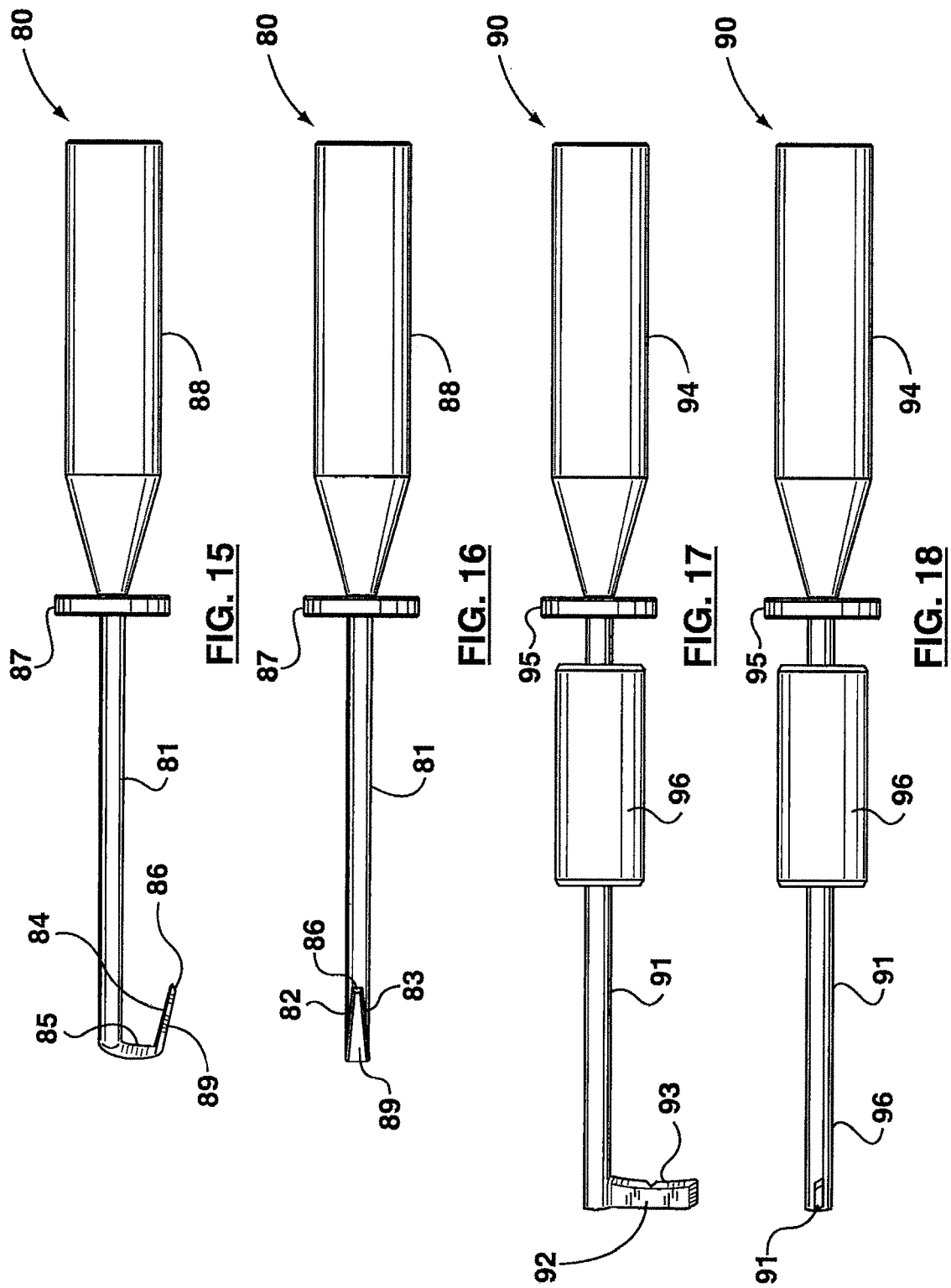

MEDICAL IMPLANT EXTRACTION DEVICE

CROSS-REFERENCE TO RELATED APPLICATIONS

This application is a continuation of U.S. patent application Ser. No. 13/080,620 filed on Apr. 5, 2011 entitled "Medical Implant Extraction Device", which claims the benefit of U.S. Provisional Patent Application No. 61/341,785 filed on Apr. 5, 2010 and which is incorporated by reference in its entirety.

TECHNICAL FIELD

The subject matter described herein relates in general to devices and systems for use in orthopedic surgery, and more particularly to revision arthroplasty.

BACKGROUND

Arthroplasty is a surgical procedure in which an arthritic or dysfunctional joint surface is replaced with an orthopedic prosthesis. By way of example, in a total knee arthroplasty, the patient's femoral and tibial bones are contoured for receiving prosthetic implants, and three component prosthetic parts (femoral, tibial, and patella) are implanted.

For optimal function, a strong bond between the patient's natural bone and the metal or plastic components of the implanted prosthesis must be achieved. Fixation features such as cement (e.g. methyl methacrolate compounds), surface textures that enhance natural bone ingrowth, and/or fixation pegs or similar structures are typically employed to achieve this strong bond.

If an implant fails to function correctly or becomes infected, revision surgery (known as revision arthroplasty) is normally required. Revision arthroplasty generally involves the removal of a previously-implanted prosthetic joint, and the replacement thereof with a new prosthesis. During this procedure, the surgeon may remove some or all of the implanted component parts of the affected prosthesis.

Removal of the previously-implanted prosthesis requires disruption of the strong existing bone-to-prosthesis bond (which may be facilitated or enhanced by fixation features of the sort described above), and the proximity of vulnerable anatomic structures such as blood vessels and nerves in the typically tight confines of space within which the disruptive force must be applied may pose difficulties for the surgeon and may make removal of the implanted components potentially hazardous to the patient. In particular, since the disruption of all or a portion of the bone-to-prosthesis bond typically occurs rather suddenly, it is not uncommon at the moment of disruption for the instrument that is being used to apply the disruptive force to move in the direction of the force applied in a somewhat uncontrolled manner for a variable distance, despite the best efforts and skill of the operating surgeon to limit this movement.

Various design characteristics of prosthetic implants and other circumstances may further exacerbate these difficulties and hazards, including the three-dimensional configuration of the prosthetic implants, the existence of a multiplicity of different sizes of prosthetic implants, and the buildup of scar tissue around a previously-implanted prosthesis, which can make it difficult to gain the necessary exposure of the bonded interface between natural bone and implanted component. The overall complexity associated with the safe removal of implants using known instruments and methods may accordingly result in a long operative procedure and consequent long duration of anaesthetic administered to the patient.

The three-dimensional configuration of a prosthetic implant is generally selected so as to optimize the functionality of the implant, as well as the ability to achieve a strong bone-to-prosthesis bond. The bone-contacting surface of a prosthetic implant component may accordingly comprise complex shapes that include curved, angled and flat surfaces of various dimensions, as well as pegs or other fixation features of the sort discussed above, which co-operate with complementary bone surface features and structure that are created by the surgeon to accept the component during implantation. By way of example, the tibial component of a knee joint prosthesis may include multiple pegs or a broad single stem, or a combination thereof.

Heretofore, the orthopedic instruments that have been used by orthopedic surgeons to remove implanted prosthetic components during a revision arthroplasty have included thin flexible single end cutting osteotomes, solid single end cutting osteotomes, jiggly saws, oscillating saws and reciprocating saws. These instruments are in many cases functionally limited in that they are either too broad, too thick and/or otherwise unable to fit within the tight confines of a typical revision arthroplasty. Their use therefore, although necessary, challenges the surgeon's abilities to deliver strong but controlled forces in a variety of directions, as is usually required to disrupt the bond, but to limit unwanted residual movement of the cutting edge immediately after disruption occurs. The use of these known instruments may accordingly also result in the removal of excess quantities of the patient's essential bone during a revision arthroplasty, leaving undesirably large cavities or bone gaps that could potentially compromise the success of the revision surgery. When removing pre-existing implants which have been in the patient for a number of years, maximization of bone preservation is especially important.

Prior-known osteotomes are typically used during revision arthroplasty in a chisel-like fashion, accomplished primarily by the application of force in an axial manner using a mallet or similar instrument to strike the distal end of the osteotome and thereby to drive the knife end thereof between the prosthetic component and the host bone. Multiple blows, usually of increasing force, are typically required to weaken and eventually disrupt the bone-to-prosthesis bond. However, as noted above, when the bond is finally broken by the repetitive hammer applications, the residual axial force after disruption may result in a sudden and somewhat uncontrolled movement of the cutting surface of the osteotome in the direction of the applied force. With currently known orthopedic instruments, including osteotomes and saws, this direction of applied force (and the resulting possible uncontrolled movement) is typically towards body of the patient and the important anatomical structures within (e.g. the blood vessels and nerves at the back of a knee joint), thereby increasing the risk of inadvertent injury.

There is accordingly a need for effective devices and methods for use in orthopedic surgery that may simplify and/or expedite the progress of a revision arthroplasty while minimizing the risk of inadvertent injury and/or the removal of excess host bone. In addition, there is a need for a universal system, assembly or kit of orthopedic devices that facilitates safe, controlled prosthetic component removal, and that is applicable to all or a variety of different implanted component prosthetic designs.

SUMMARY

This summary is not an extensive overview intended to delineate the scope of the subject matter that is described and claimed herein. The summary presents aspects of the subject matter in a simplified form to provide a basic understanding thereof, as a prelude to the detailed description that is presented below.

Embodiments of the subject matter described and claimed herein provide devices and methods for use in the disruption of a bone-to-prosthesis bond during revision arthroplasty. The devices generally comprise extraction instruments that are shaped and configured to fit within the typically tight confines in which revision arthroplasty is performed, and to enhance the surgeon's control over the axis, quantum and speed of the force that must be applied to disrupt the bond. This enables the surgeon to complete the revision arthroplasty more quickly, and with reduced risk that unwanted movements might cause accidental injury to nearby vital structures. The presently disclosed devices are fabricated of stainless steel, titanium, or any other material known to those of skill in the art to be suitable for the construction of surgical instruments, and may also be inherently safer than prior-known osteotomes in that the cutting edges thereof need not be as sharp as those of prior-known osteotomes.

In some embodiments, the described devices enable the application of reverse axial forces (i.e. in a direction that is away from the body of the patient) and/or make use of pivot points provided in the shaft or the extraction blades thereof in order to interact with the implanted prosthesis directly, and thereby to provide leverage and mechanical advantage, and improved control to reduce the risk of inadvertent injury and/or excess bone loss. Varying cross-sections of the extraction blades, such as for example convex or skewed convex cross-sections, may also be provided in some embodiments in order to further enhance the surgeon's control over the accurate application and direction of disruptive forces by providing a positive directional bias towards the underside of the implanted prosthesis, and by reducing the contact surface area between the device and implant during use.

In one preferred embodiment, the device comprises a generally hook or J-shaped extraction instrument comprising an elongate shaft having a distal end and a proximal end, and an elongate reverse extraction blade connected to and spaced apart from the distal end of the shaft by a bridge, the reverse extraction blade being generally planar or convex in cross-section and extending from the bridge generally parallel to and back in the direction towards the proximal end of the shaft, and comprising at least one cutting edge disposed at the free end thereof. The extraction blade may be inclined at between roughly 0° and 45° relative to the longitudinal axis of the shaft, and may preferably further comprise additional cutting edges disposed along either or both of its longitudinal surfaces.

In another preferred embodiment, the device comprises a generally L-shaped extraction instrument comprising an elongate shaft having a distal end and a proximal end, and a generally planar reverse extraction blade connected to the distal end of the shaft and extending generally perpendicularly therefrom. The reverse extraction blade of this embodiment has at least one cutting edge along the edge of the blade that is closest to the proximal end of the shaft, and this at least one cutting edge may be angled inwards towards the shaft at an angle of between roughly 75° to 120° in order to reduce the tendency of the L-shaped extraction instrument to slip perpendicularly during use. A notch may also in some embodiments be formed in the cutting edge to facilitate pivotal action of the L-shaped extraction instrument relative to selected features of an implanted prosthetic component.

In other embodiments, the devices comprise extraction instruments, each of which comprise an elongate shaft having a distal end and a proximal end, a pivot edge formed at or near the distal end of the shaft, and an elongate extraction blade connected to the pivot edge at one of a variety of inclinations and angles with respect thereto. The elongate extraction blades of each of these embodiments have at least one cutting edge along at least one longitudinal surface thereof, and are relatively short as compared to the length of the shaft in order that pivotal movement of the cutting instrument about the pivot edge will provide readily controllable leverage and mechanical advantage to the user. A range of extraction instruments having different relative lengths of shafts and elongate extraction blades may be provided, depending on the leverage and space requirements of varying applications.

The elongate shaft of the extraction instrument may further comprise a handle element at or near its proximal end. The handle may be integral with the elongate shaft, or may alternatively be formed separately from the cutting instrument and either permanently affixed or removably connected at or near the proximal end of the shaft in any of the many suitable manners known to those of skill in the art to provide a positive engagement in both an axial and rotational sense. In embodiments where the handle is formed separately from the extraction instrument, the handle may be fabricated of the same material as the extraction instrument, or from any other material known to those of skill in the art to be suitable for the construction of surgical instruments.

In some preferred embodiments, the device further comprises a reverse force hammer (conventionally known as a "slap hammer") that includes a movable weight with an interior aperture sized for the slidable engagement of the shaft of the extraction instrument, and which is limited in its range of travel towards the distal end of the shaft by either the handle or by a separate striking plate connected to either the handle or to the shaft of the extraction instrument. When the slap hammer is moved sharply towards the proximal end of the shaft and collides with either the handle or the striking plate, a force is applied along the axis of the extraction instrument in the proximal direction. This force is 180° reversed from the force that is normally applied to a prior-known osteotome by a conventional hammer.

Also described and claimed herein is a system, assembly and kit of extraction instruments, each extraction instrument having a different extraction blade, and each extraction instrument facilitating the application of disruptive force in a previously undisclosed manner with associated functional advantages as described in further detail herein below. For convenience, the claimed subject matter is described by way of example but not limitation in the detailed description provided below in relation to a system of devices suitable for use primarily in revision knee arthroplasty. However, it would of course be readily apparent to those of skill in the art that the advantages afforded by the subject matter that is described and claimed herein are not limited to any specific joint revision.

BRIEF DESCRIPTION OF THE DRAWINGS

For a fuller understanding of the nature and advantages of the disclosed subject matter, as well as the preferred mode of use thereof, reference should be made to the following detailed description, read in conjunction with the accompanying drawings. In the drawings, like reference numerals designate like or similar steps or components.

FIG. 15 is a top plan view of an extraction instrument in accordance with an embodiment of the disclosed subject matter, shown in combination with a handle and strike plate.

FIG. 16 is front elevation of the extraction instrument of FIG. 15.

FIG. 17 is a top plan view of an extraction instrument in accordance with an embodiment of the disclosed subject matter, shown in combination with a handle, strike plate and slap hammer.

FIG. 18 is front elevation of the extraction instrument of FIG. 17.

DETAILED DESCRIPTION OF SPECIFIC EMBODIMENTS

As previously noted, the claimed subject matter is illustrated and described herein by way of example but not limitation in relation to a system of devices suitable for use primarily in revision arthroplasty of a knee joint. However, it would of course be readily apparent to those of skill in the art that the advantages afforded by the subject matter that is described and claimed herein are not limited to any specific joint revision.

Figure 1:
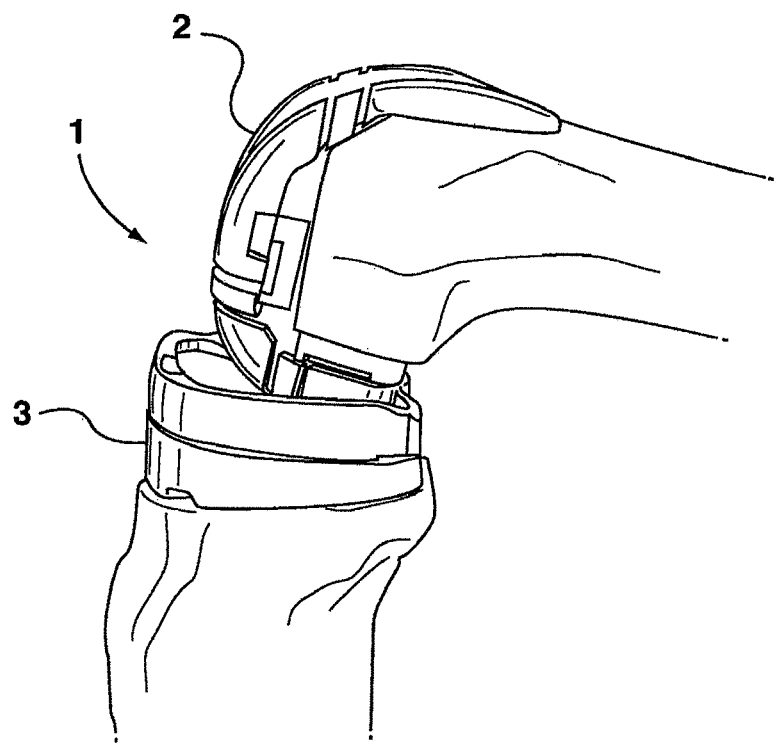
FIG. 1 is a perspective view of a representative knee joint prosthesis illustrating the relative placement of implanted femoral and tibial prosthetic components.
Figure 2:
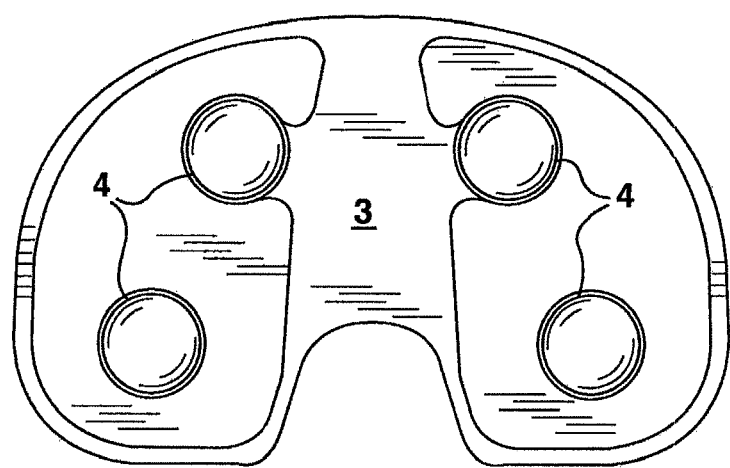
FIG. 2 is a bottom plan view of a representative tibial prosthetic component illustrating a typical arrangement of fixation pegs.

FIG. 1 illustrates representative a knee joint prosthesis 1 showing the relative placement of implanted femoral prosthetic component 2 and tibial prosthetic component 3, and FIG. 2 is a bottom plan view of a representative tibial prosthetic component 3 illustrating a typical arrangement of fixation pegs 4.

Six representative extraction instruments are illustrated in FIGS. 3-14, each of which is shaped and configured to fit within the typically tight confines in which revision arthroplasty is performed, and to enhance the surgeon's control over the axis, quantum and speed of the force that must be applied to disrupt the strong bond that exists between a previously-implanted prosthetic component and the host bone of the patient. Other configurations of extraction instruments that are within the scope of the present disclosure will, of course, be readily apparent to those of skill in the art from an understanding of the principles that underlie the presently-disclosed subject matter.

Figure 3:
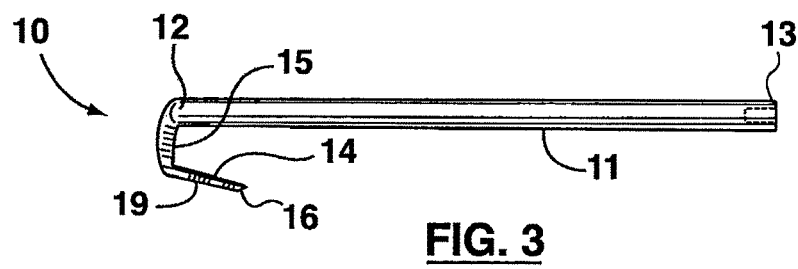
FIG. 3 is a top plan view of an extraction instrument in accordance with an embodiment of the disclosed subject matter.
Figure 4:
FIG. 4 is front elevation of the extraction instrument of FIG. 3.

With reference to FIGS. 3 and 4, there is illustrated a generally hook or J-shaped extraction instrument 10 comprising an elongate shaft 11 having a distal end 12 and a proximal end 13, and an elongate reverse extraction blade 14 connected to and spaced apart from the distal end 12 of the shaft 11 by a bridge 15. The reverse extraction blade 14 extends from the bridge 15 generally parallel to and back in the direction towards proximal end 13 of the shaft 11, and comprises sharp tip 16 and tapered sharp lateral edges 17 and 18.

The surface 19 of reverse extraction blade 14 is generally planar to slightly convex or skewed convex, with convex and skewed convex configurations providing a positive directional bias towards the underside of the implant during use, as well as reducing the contact surface area of the reverse extraction blade 14. Alternative representative embodiments of each of the generally planar, convex and skewed convex cross-sections of reverse extraction blade 14 are illustrated, respectively, in FIGS. 20A-20H.

The elongate reverse extraction blade 14 may be inclined between roughly 0° and 45° relative to the longitudinal axis of the shaft 11, and extraction instrument 10 may optionally further comprise a connector 19A at the proximal end 13 of shaft 11 for connection to a strike plate and/or handle, as will be further described below.

The extraction instrument 10 is fabricated of stainless steel, titanium, or any other material known to those of skill in the art to be suitable for the construction of surgical instruments, and in preferred embodiments that are useful in revision arthroplasty of the knee joint, reverse extraction blade 14 may be between about 0.5 mm to 5 mm thick, between about 5 mm to 35 mm long, and between about 3 mm to 20 mm wide where it connects to the bridge 15, tapering down to about 19 mm to 0.1 mm in width at sharp tip 16. The bridge 15 may separate the shaft 11 and reverse extraction blade 14 by between about 2 mm to 20 mm, and may be flat or rounded (i.e. convex or concave) in cross-section to facilitate pivoting of the reverse extraction blade 14 against the outer and inner edges or other features of the prosthetic component to be removed.

The cross-section of shaft 11 is preferably round but may be of any other shape, and the overall dimension of the cross-section may range from about 2 mm to 10 mm. The length of shaft 11 may range from about 20 mm to 300 mm, and in any event will be selected to be sufficiently long to provide suitable access to the prosthetic component to be removed.

Figure 5:
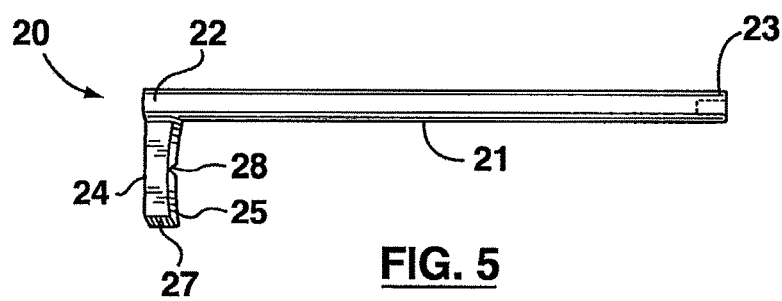
FIG. 5 is a top plan view of an extraction instrument in accordance with an embodiment of the disclosed subject matter.
Figure 6:
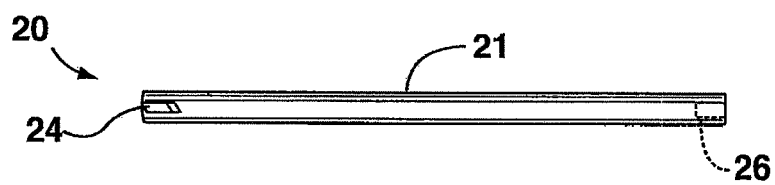
FIG. 6 is front elevation of the extraction instrument of FIG. 5.

FIGS. 5 and 6 illustrate a generally L-shaped extraction instrument 20 comprising an elongate shaft 21 having a distal end 22 and a proximal end 23, and a generally planar reverse extraction blade 24 connected to the distal end 22 of the shaft 21 and extending generally perpendicularly therefrom. The reverse extraction blade 24 has at least one tapered sharp edge 25 along the edge of the blade 24 that is closest to the proximal end 23 of the shaft 21, and this at least one sharp edge 25 is preferably angled inwards towards the shaft 21 at an angle of between roughly 75° to 120° in order to reduce the tendency of the L-shaped extraction instrument to slip perpendicularly during use. L-shaped extraction instrument 20 may optionally further comprise a connector 26 at the proximal end 23 of shaft 21 for connection to a strike plate and/or handle, as will be further described below.

The extraction instrument 20 is fabricated of stainless steel, titanium, or any other materials known to those of skill in the art to be suitable for the construction of surgical instruments, and in preferred embodiments useful in revision arthroplasty of the knee joint, reverse extraction blade 24 may be between about 0.5 to 5 mm in thickness, between about 5 mm and 30 mm wide, and between about 3 mm to 15 mm in depth. The free edge 27 of reverse extraction blade 24 is preferably flat, and a symmetrical or asymmetrical notch 28 may be provided in sharp edge 25 of reverse extraction blade 24, or elsewhere on reverse extraction blade 24, in order to facilitate leveraging of extraction instrument 20 in relation to a fixation peg 4 or other surface feature of an implanted prosthetic component.

The cross-section of shaft 21 is preferably round but may be of any other shape, and the overall dimension of the cross-section may range from about 2 mm to 10 mm. The length of shaft 21 may range from about 20 mm to 300 mm, and in any event will be selected to be sufficiently long to provide suitable access to the prosthetic component to be removed.

FIGS. 7-13 illustrate four representative embodiments of extraction instruments in which a pivot edge is provided at or near the distal end of the shaft in order to facilitate the pivotal movement of the extraction instrument relative to a surface feature of the implanted prosthesis to be extracted, and thereby to provide increased mechanical advantage and improved control in the application of the force necessary to disrupt the bone-to-prosthesis bond. The four representative embodiments that are illustrated are preferred in relation to the revision arthroplasty of a knee joint, but as would be apparent to those of skill in the art, other configurations that are within the scope of the present disclosure are also possible. By way of example, the pivot point of an extraction instrument may be located at some other location on the shaft, and may for example comprise a symmetrical or asymmetrical "notch" configured to interact with selected surface features of an implanted prosthetic component.

Figure 7:
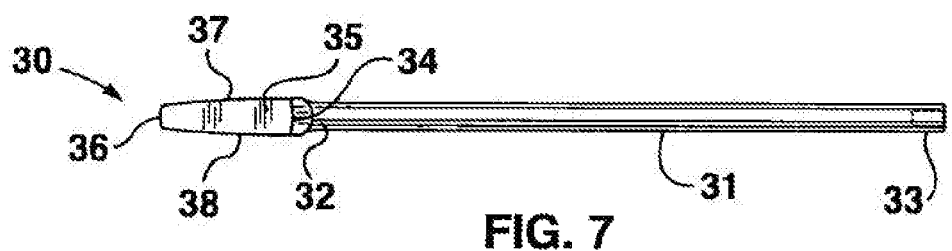
FIG. 7 is a top plan view of an extraction instrument in accordance with an embodiment of the disclosed subject matter.
Figure 8:
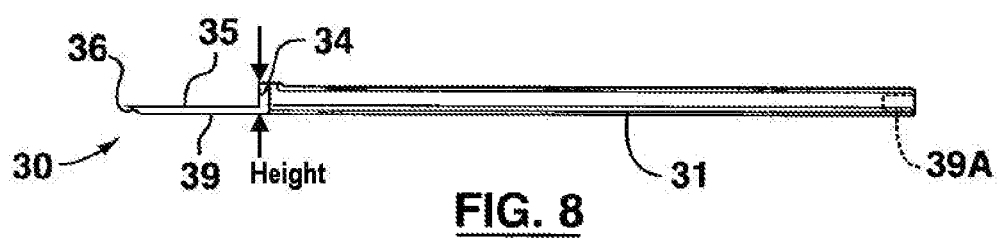
FIG. 8 is front elevation of the extraction instrument of FIG. 7.

With reference to FIGS. 7 and 8, there is illustrated an extraction instrument 30 comprising an elongate shaft 31 having a distal end 32 and a proximal end 33. A pivot edge 34 is formed at the distal end 32 of the shaft 31, and may be of generally convex, concave or planar configuration. A straight elongate extraction blade 35 comprising sharp or blunt tip 36 and tapered sharp lateral edges 37 and 38 is connected at roughly a right angle to the face of the pivot edge 34, and extends in the distal direction generally collinearly along the longitudinal axis of shaft 31. The straight elongate extraction blade 35 may, however, also extend in some embodiments along a longitudinal axis that is offset from that of shaft 31 so as to enhance clearance. The surface 39 of straight elongate extraction blade 35 is generally planar, convex or skewed convex in cross-section, with convex configurations providing a positive directional bias towards the underside of the implant during use, as well as reducing the contact surface area of the straight elongate extraction blade 35. Alternative representative embodiments of each of the generally planar, convex and skewed convex cross-sections of straight elongate extraction blade 35 are illustrated, respectively, in FIGS. 20A-20H. Extraction instrument 30 may optionally further comprise a connector 39A at the proximal end 33 of shaft 31 for connection to a strike plate and/or handle, as will be further described below.

The extraction instrument 30 is fabricated of stainless steel, titanium, or any other materials known to those of skill in the art to be suitable for the construction of surgical instruments, and in preferred embodiments useful in revision arthroplasty of the knee joint, straight elongate extraction blade 35 may be between about 0.5 mm to 5 mm thick, between about 5 mm to 60 mm long, and between about 3 mm to 20 mm wide where it connects to the pivot edge 34, tapering down to about 19 mm to 0.1 mm in width at tip 36. The pivot edge 34 is between about 0 mm (flush) and 15 mm in height (as measured perpendicularly to the longitudinal axis of the shaft 31), and may be flat or rounded (i.e. convex or concave) to facilitate pivoting of the straight elongate extraction blade 35 against the outer and inner edges or other features of the prosthetic component to be removed.

The cross-section of shaft 31 is preferably round but may be of any other shape, and the overall dimension of the cross-section may range from about 2 mm to 10 mm. The length of shaft 31 may range from about 20 mm to 300 mm, and in any event will be selected to be sufficiently long to provide suitable access to the prosthetic component to be removed.

Figure 9:
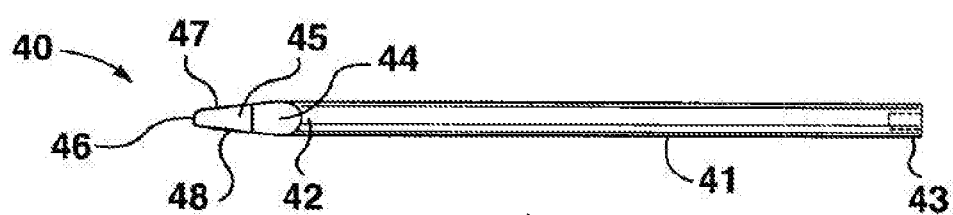
FIG. 9 is a top plan view of an extraction instrument in accordance with an embodiment of the disclosed subject matter.
Figure 10:
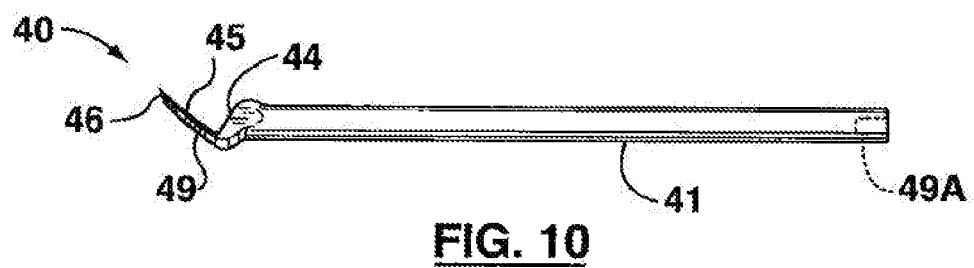
FIG. 10 is front elevation of the extraction instrument of FIG. 9.

FIGS. 9 and 10 illustrate an extraction instrument 40 comprising an elongate shaft 41 having a distal end 42 and a proximal end 43. A pivot edge 44 is formed at the distal end 42 of the shaft 41 at an angle relative to the longitudinal axis of the shaft 41, and may be of generally convex, concave or flat configuration. An elongate extraction blade 45 comprising tip 46 and tapered sharp lateral edges 47 and 48 is connected at roughly a right angle to the face of the pivot edge 44 and extends in the distal direction at an angle through the longitudinal axis of the shaft 41. The surface 49 of elongate extraction blade 45 is generally planar, convex or skewed convex in cross-section, with convex configurations providing a positive directional bias towards the underside of the implant during use, as well as reducing the contact surface area of the elongate extraction blade 45. Alternative representative embodiments of each of the generally planar, convex and skewed convex cross-sections of elongate extraction blade 45 are illustrated, respectively, in FIGS. 20A-20H. Extraction instrument 40 may optionally further comprise a connector 49A at the proximal end 43 of shaft 41 for connection to a strike plate and/or handle, as will be further described below.

The extraction instrument 40 is fabricated of stainless steel, titanium, or any other materials known to those of skill in the art to be suitable for the construction of surgical instruments, and in preferred embodiments useful in revision arthroplasty of the knee joint, elongate extraction blade 45 may be between about 0.5 mm to 5 mm thick, between about 5 mm to 25 mm long, and between about 3 mm to 15 mm wide where it connects to the pivot edge 44, tapering down to about 14 mm to 0.1 mm in width at tip 46. The pivot edge 44 is between about 0 mm (flush) and 15 mm in height (as measured perpendicularly to the longitudinal axis of the shaft 41), and may be flat or rounded (i.e. convex or concave) to facilitate pivoting of the elongate extraction blade 45 against the outer and inner edges of the prosthetic component to be removed.

The cross-section of shaft 41 is preferably round but may be of any other shape, and the overall dimension of the cross-section may range from about 2 mm to 10 mm. The length of shaft 41 may range from about 20 mm to 300 mm, and in any event will be selected to be sufficiently long to provide access to the prosthetic component to be removed.

Figure 11:
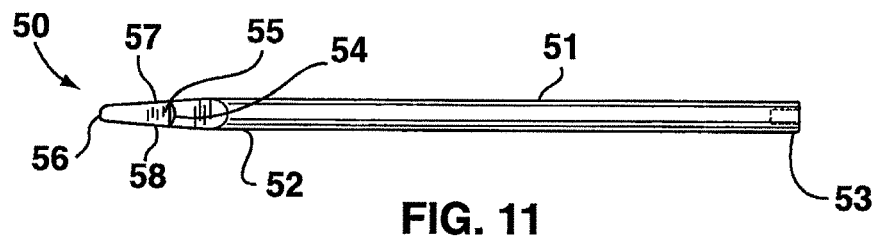
FIG. 11 is a top plan view of an extraction instrument in accordance with an embodiment of the disclosed subject matter.
Figure 12:
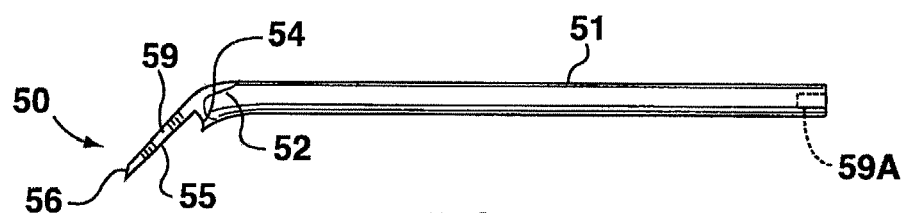
FIG. 12 is front elevation of the extraction instrument of FIG. 11.

FIGS. 11 and 12 illustrate an extraction instrument 50 comprising an elongate shaft 51 having a distal end 52 and a proximal end 53. Distal end 52 of shaft 51 is curved at an angle relative to the overall longitudinal axis of the shaft 51, and has a pivot edge 54 formed at the end thereof. The pivot edge 54 may be of convex, concave or flat configuration, and an elongate extraction blade 55 comprising tip 56 and tapered sharp lateral edges 57 and 58 is connected at roughly a right angle to the face of the pivot edge 54 and extends in the distal direction at an angle through the longitudinal axis of the shaft 51. The surface 59 of elongate extraction blade 55 is generally planar, convex or skewed convex in cross-section, with convex configurations providing a positive directional bias towards the underside of the implant during use, as well as reducing the contact surface area of the straight elongate extraction blade 55. Alternative representative embodiments of each of the generally planar, convex and skewed convex cross-sections of elongate extraction blade 55 are illustrated, respectively, in FIGS. 20A-20H. Extraction instrument 50 may further optionally comprise a connector 59A at the proximal end 53 of shaft 51 for connection to a strike plate and/or handle, as will be further described below.

The extraction instrument 50 is fabricated of stainless steel, titanium, or any other materials known to those of skill in the art to be suitable for the construction of surgical instruments, and in preferred embodiments useful in revision arthroplasty of the knee joint, elongate extraction blade 55 may be between about 0.5 mm to 5 mm thick, between about 5 mm to 25 mm long, and between about 3 mm to 15 mm wide where it connects to the pivot edge 54, tapering down to about 14 mm to 0.1 mm in width at tip 56. The pivot edge 54 is between about 0 mm (flush) and 15 mm in height (as measured perpendicularly to the longitudinal axis of the shaft 51), and may be flat or rounded (i.e. convex or concave) to facilitate pivoting of the elongate extraction blade 55 against the outer and inner edges or other features of the prosthetic component to be removed. As illustrated in FIG. 12, pivot edge 54 may also be "hook-shaped" in order to reduce the possibility of slippage of the extraction instrument 50 relative to blade the prosthetic component during the application of force. The pivot edges of other embodiments of the extraction instrument may similarly be "hook-shaped" in configuration.

The cross-section of shaft 51 is preferably round but may be of any other shape, and the overall dimension of the cross-section may range from about 2 mm to 10 mm. The length of shaft 51 may range from about 20 mm to 300 mm, and in any event will be selected to be sufficiently long to provide access to the prosthetic component to be removed.

Figure 13:
FIG. 13 is a top plan view of an extraction instrument in accordance with an embodiment of the disclosed subject matter.
Figure 14:
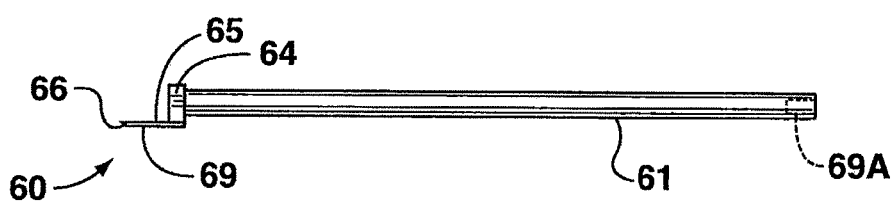
FIG. 14 is front elevation of the extraction instrument of FIG. 13.

FIGS. 13 and 14 illustrate an extraction instrument 60 comprising an elongate shaft 61 having a distal end 62 and a proximal end 63. A pivot edge 64 is formed at the distal end 62 of the shaft 61, and may be convex, concave or flat configuration. A side angled elongate extraction blade 65 comprising tip 66 and tapered sharp lateral edges 67 and 68 is connected at between roughly 0° and 90°, and most preferably around 45° laterally relative to the longitudinal axis of the shaft 61, and at roughly a right angle to the face of the pivot edge 64. The surface 69 of side angled elongate extraction blade 65 is generally planar, convex or skewed convex in cross-section, with convex configurations providing a positive directional bias towards the underside of the implant during use, as well as reducing the contact surface area of the straight elongate extraction blade 65. Alternative representative embodiments of each of the generally planar, convex and skewed convex cross-sections of side angled elongate extraction blade 65 are illustrated, respectively, in FIGS. 20A-20H. Extraction instrument 60 may further optionally comprise a connector 69A at the proximal end 63 of shaft 61 for connection to a strike plate and/or handle, as will be further described below.

The extraction instrument 60 is fabricated of stainless steel, titanium, or any other materials known to those of skill in the art to be suitable for the construction of surgical instruments, and in preferred embodiments useful in revision arthroplasty of the knee joint, and side angled elongate extraction blade may be between about 0.5 mm to 5 mm thick, between about 5 mm to 25 mm long, and between about 3 mm to 20 mm wide where it connects to the pivot edge 64, tapering down to about 19 mm to 0.1 mm in width at sharp tip 66. The pivot edge 64 is between about 0 mm (flush) and 15 mm in height (as measured perpendicularly to the longitudinal axis of the shaft 41), and may be flat or rounded (i.e. convex or concave) to facilitate pivoting of the elongate extraction blade 65 against the outer and inner edges or other features of the prosthetic component to be removed.

The cross-section of shaft 61 is preferably round but may be of any other shape, and the overall dimension of the cross-section may range from about 2 mm to 10 mm. The length of shaft 61 may range from about 20 mm to 300 mm, and in any event will be selected to be sufficiently long to provide access to the prosthetic component to be removed.

As previously described, the extraction instruments of FIGS. 3-14 may further comprise integrally formed handle and/or strike plate elements at or near their proximal ends, or may alternatively be configured with a suitable connector (i.e. connector 19A, 26, 39A, 49A, 59A or 69A) at or near their proximal ends for the permanent or removable connection of a separately-formed strike plate and/or handle. The connection may be effected in any conventional manner known to those of skill in the art to provide a positive engagement in both an axial and rotational sense. By way of example, complementary male and female threads may be provided in the handle and at the proximal end of the extraction instrument shaft in order to provide a positive engagement in an axial sense, and complementary protrusions and mating recesses or the like may also be provided in the handle and at the proximal end of the extraction instrument shaft to provide rotational stabilization.

In some preferred embodiments, particularly in relation to embodiments in which the extraction instrument comprises a reverse extraction blade, a reverse force hammer (conventionally known as a "slap hammer") that comprises a movable weight with an interior aperture sized for the slidable engagement of the shaft of the extraction instrument, and which is limited in its range of travel towards the proximal end of the shaft by the handle or by a separate striking plate connected to either the handle or to the shaft of the extraction instrument, may also be also provided. Alternatively, connectors 19A, 26, 39A, 49A, 59A and/or 69A may be configured for attachment of a conventional slap hammer assembly. The strike plate, handle and/or slap hammer may be fabricated from the same material as the cutting instruments, or from any material known to those of skill in the art to be suitable for the construction of surgical instruments.

FIGS. 15 and 16 illustrate a representative assembly of the extraction instrument of FIGS. 3 and 4 in combination with a strike plate and handle, and FIGS. 17 and 18 illustrate a representative assembly of the extraction instrument of FIGS. 5 and 6 in combination with a strike plate, handle and slap hammer. Although not illustrated, it would of course be readily apparent to those of skill in the art that assemblies of the extraction instruments of FIGS. 7 through 14 together with handles, strike plates and/or slap hammers may similarly be constructed.

In FIGS. 15 and 16, the combination J-shaped extraction instrument, strike plate and handle are generally indicated by reference numeral 80. Combination instrument 80 comprises an elongate shaft 81 having an elongate reverse extraction blade 84 connected to and spaced apart from a first end of the shaft 81 by a bridge 85. Strike plate 87 and handle 88 are attached permanently or releasably via connector 19A (see FIG. 4) at the second end of shaft 81 and mating connectors on each of the strike plate 87 and handle 88. Alternatively, as discussed above, strike plate 87 and/or handle 88 may be formed integrally with shaft 81.

As with the extraction instrument of FIGS. 3 and 4, the elongate reverse extraction blade 84 extends from the bridge 85 generally parallel to and back in the direction towards the second end and the strike plate 87 and handle 88, and comprises tip 86 and tapered sharp lateral edges 82 and 83. The surface 89 of reverse extraction blade 84 is generally planar to slightly convex or skewed convex, with convex configurations providing a positive directional bias towards the underside of the implant during use, as well as reducing the contact surface area of the reverse extraction blade 84. Alternative representative embodiments of each of the generally planar, convex and skewed convex cross-sections of reverse extraction blade 84 are illustrated, respectively, in FIGS. 20A-20H.

A combination L-shaped extraction instrument, strike plate, handle and slap hammer is generally indicated by reference numeral 90 in FIGS. 17 and 18. Combination instrument 90 comprises an elongate shaft 91 having a generally planar reverse extraction blade 92 connected to a first end of the shaft 91, and a handle 94 and strike plate 95 attached permanently or releasably via connector 26 (see FIG. 6) at the second end of shaft 91 and mating connectors on each of the handle 94 and strike plate 95. Slap hammer 96 comprises a movable weigh that is slidably engaged on shaft 91 and limited in its range of travel towards the second end of shaft 91 by the strike plate 95 and/or handle 94. In alternative embodiments, such as where additional room for travel of slap hammer 96 is desired, the combination extraction instrument may comprise only a strike plate (i.e. without a handle) attached at the second end of shaft 91.

The reverse extraction blade 92 has at least one tapered sharp edge 93 along the edge of the blade 92 that is closest to the second end of the shaft 91, and this at least one sharp edge 93 is preferably beveled or tapered inwards towards the shaft 91 at an angle of between roughly 75° to 120° in order to reduce the tendency of the L-shaped extraction instrument to slip perpendicularly during use, such as when the slap hammer 96 is moved sharply towards the second end of the shaft 91 and collides with either the striking plate 95 or handle 94.

Figure 19:
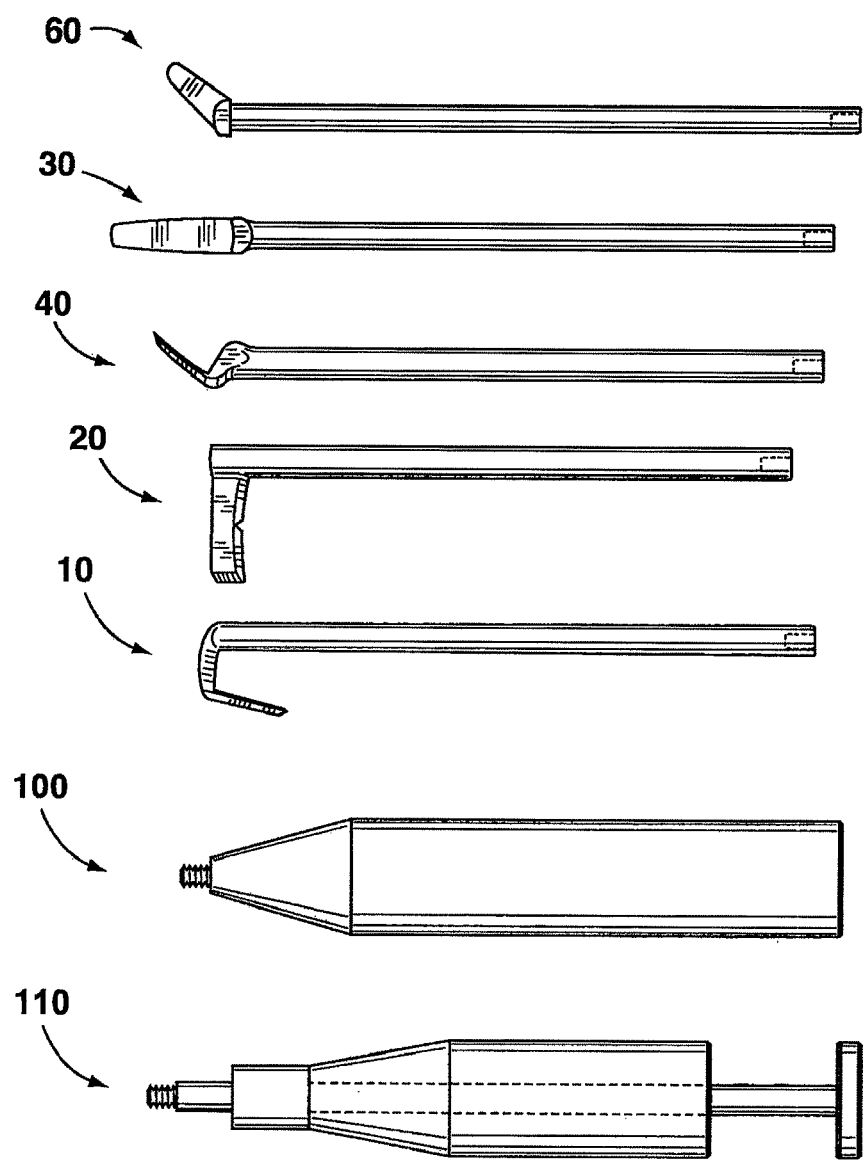
FIG. 19 is a top plan view of a representative system or kit of extraction instruments suitable for use primarily in revision knee arthroplasty.
Figure 20A:
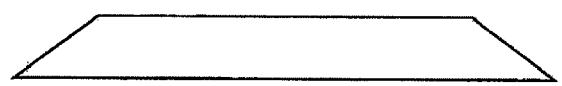
FIGS. 20A-20H are enlarged cross-sectional end views of the extraction blade of extraction instruments in accordance with embodiments of the disclosed subject matter.
Figure 20B:
Figure 20C:
Figure 20D:
Figure 20E:
Figure 20F:
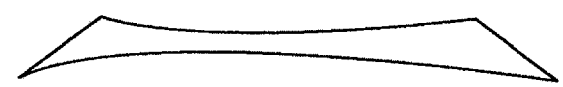
Figure 20G:
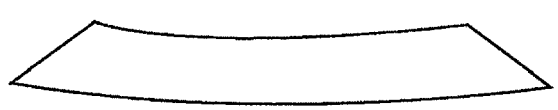
Figure 20H:
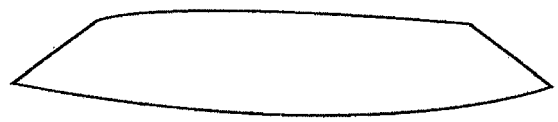

Referring now to FIG. 19, there is illustrated in a top plan view a representative system and kit of extraction instruments suitable for use primarily in revision knee arthroplasty. The system and kit comprise J-shaped reverse extraction instrument 10 of FIG. 3, the L-shaped extraction instrument 20 of FIG. 5, and one or more of each of pivotal extraction instruments 30, 40 and 60 of FIGS. 7, 9 and 13, respectively. Also included in the system and kit are one or more of each of detachable handle 100 and slap hammer 110. In combination, the components of the system and kit of FIG. 19 facilitate the ability of a surgeon to apply controlled forces in a variety of axes, including reverse, and to utilize a variety of pivot points in conjunction with the implanted components being removed in order to provide controlled leverage and mechanical advantage, and thereby enhance both the speed and safety of a knee revision arthroscopy. Of course, as would be readily apparent to those of skill in the art from an understanding of the principles that underlie the presently-disclosed subject matter, other systems and kits that include more, fewer or different component parts (such as, for example, integral combination extraction instruments), and systems intended to be particularly suitable for the revision arthroscopy of various other joints may be constructed.

FIGS. 21-28 illustrate in representative fashion the application of reverse cutting edges and forces, and the use of a variety of pivot points to enhance control in the application of forces in the engagement of representative examples of the extraction instruments of FIGS. 3-14 and the edges, surfaces and other three-dimensional features of a prosthetic component to be removed.

Figure 21:
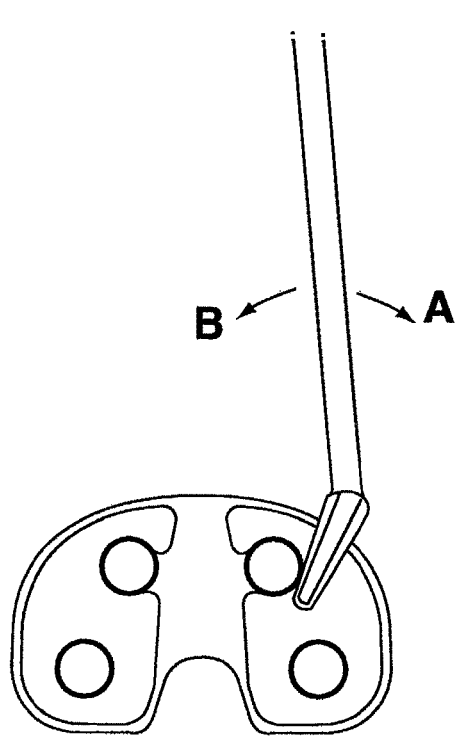
FIGS. 21-28 are representative perspective views illustrating the interaction between extraction instruments in accordance with embodiments of the disclosed subject matter and representative tibial prosthetic components.
Figure 22:
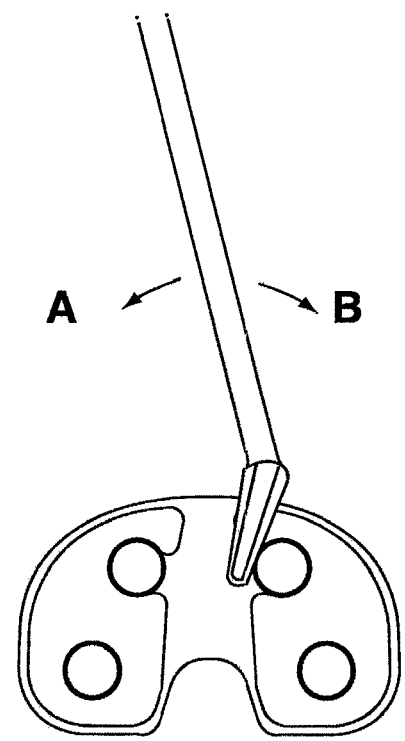
Figure 23:
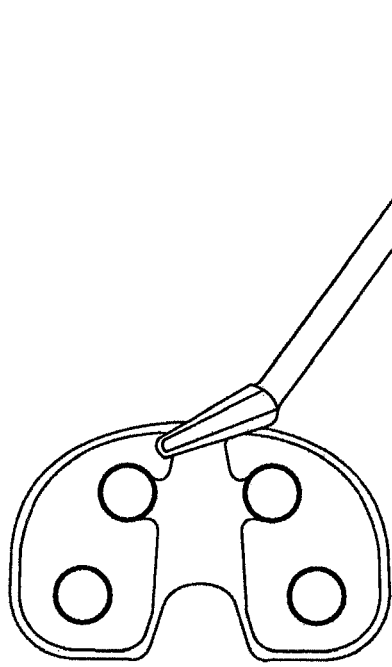

In FIGS. 21-22, the extraction instrument of FIGS. 13 and 14 is shown with its pivot edge abutting the side surface of a representative tibial prosthetic component, and with its extraction blade abutting the bottom surface of the prosthetic component as well as one of the fixation pegs of the component. In FIG. 23, the same extraction instrument is shown with the pivot edge still abutting the side surface of the prosthetic component, but with its extraction blade abutting only the bottom surface.

The fixation peg may accordingly be used in FIGS. 21 and 22, but not in FIG. 23, as a pivot point vis-à-vis the extraction blade to draw the extraction instrument generally along the bottom surface of the prosthesis in the direction marked "A", and thereby to apply a controlled force in the disruption of the bone-to-prosthesis bond adjacent to the corresponding edge of the extraction blade. Alternatively, the extraction instrument may be pivoted about its pivot edge in the direction marked "B" (in the examples of any of FIGS. 21-23) to disrupt in a controlled manner the bone-to-prosthesis bond adjacent to the opposite edge of the extraction blade. In either case, the pivotal movement of the extraction instrument relative to a surface feature of the prosthetic component facilitates increased leverage and mechanical advantage, and enables improved control in the application of the force necessary to disrupt the bone-to-prosthesis bond.

Figure 24:
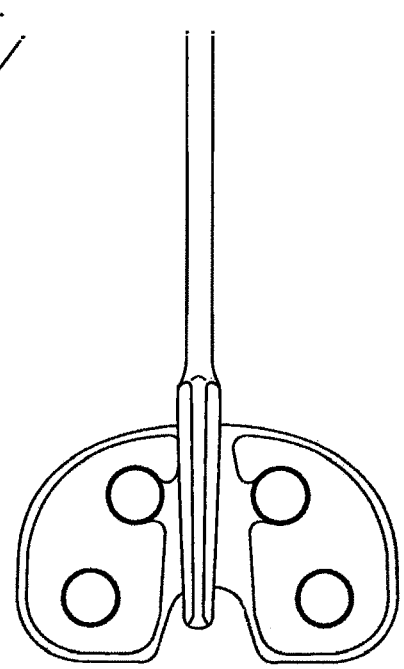
Figure 25:
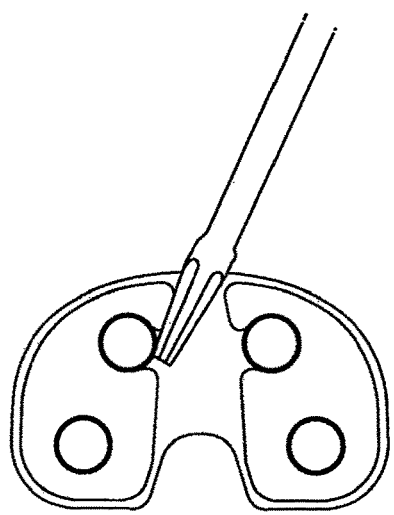
Figure 26:
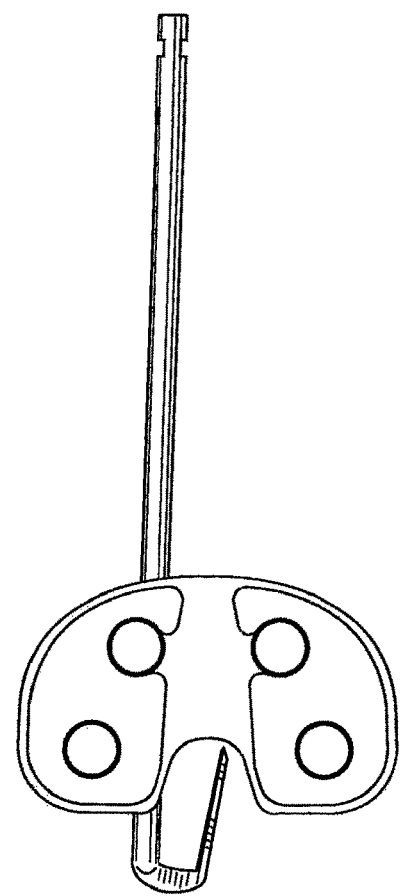
Figure 27:
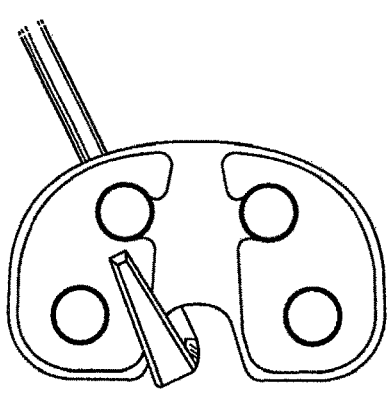
Figure 28:
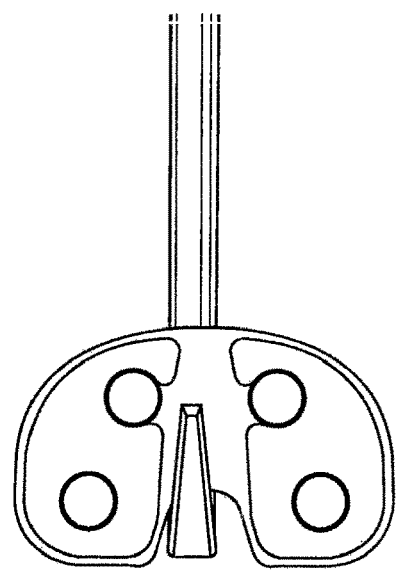

FIGS. 24 and 25 illustrate, respectively, the extraction instruments of FIGS. 7 and 8, and of FIGS. 9 and 10, engaging a representative tibial prosthetic component. As in FIGS. 21-23, the pivot edge of each extraction instrument is shown abutting the side surface of the representative prosthetic component, and pivotal movement of the extraction instrument relative to the side surface of the prosthetic component facilitates increased leverage and mechanical advantage, and thus enables improved control in the application of the necessary disruptive force. FIGS. 26-28 illustrate three representative stages of the insertion and use of the J-shaped extraction instrument of FIGS. 3 and 4 in the application of reverse axial forces in the removal of the prosthetic component in a direction that is away from the important anatomical structures (such as blood vessels and nerves) that are located in close proximity to the prosthetic component.

The present description includes the best presently contemplated mode of carrying out the subject matter disclosed and claimed herein. The description is made for the purpose of illustrating the general principles of the subject matter and not be taken in a limiting sense; the subject matter can find utility in a variety of implementations without departing from the scope of the disclosure made, as will be apparent to those of skill in the art from an understanding of the principles that underlie the subject matter.

What is claimed is:

1. An orthopedic extraction instrument for use in revision arthroplasty of a prosthetic component, the extraction instrument comprising:
    an elongate shaft having a proximal end and a distal end;
    a pivot formed at the distal end of the shaft having a rounded pivot surface directed outwardly with respect to the distal end of the shaft and perpendicular to a longitudinal axis of the elongate shaft, the rounded pivot surface having a convex lateral cross-section;
    an elongate extraction blade extending directly from said rounded pivot surface in a distal direction with respect to said shaft, the elongate extraction blade having a cutting edge disposed along each lateral edge of a surface of the blade, the surface of the blade being oriented at a right angle to the pivot surface, said rounded pivot surface being configured to engage a surface feature of the prosthetic component to facilitate lateral pivoting movement of the elongate shaft about the rounded pivot surface causing a lateral cutting action by said cutting edge for disrupting a bond between the prosthetic component and a host bone of a patient.

2. The orthopedic extraction instrument of claim 1 wherein said rounded pivot surface has a height that is between 0.5 mm and 15 mm, wherein the height is measured perpendicularly to the longitudinal axis of the shaft.

3. The orthopedic extraction instrument of claim 1 wherein said extraction blade has a cross-section that is one of flat, convex, or skewed convex.

4. The orthopedic extraction instrument of claim 1 wherein an axial length of said extraction blade is relatively short as compared to a length of said shaft.

5. The orthopedic extraction instrument of claim 1 further comprising a handle at the proximal end of said shaft.

6. The orthopedic extraction instrument of claim 5 further comprising a striking plate proximally adjacent the handle.

7. The orthopedic extraction instrument of claim 6 further comprising a slap hammer slidably engaged with said shaft proximal to said striking plate.

8. The orthopedic extraction instrument of claim 1 wherein the cutting edges taper inwardly toward a distal tip of the elongate extraction blade.

9. The orthopedic extraction instrument of claim 1 wherein the cutting edge runs along the length of the elongate extraction blade from the pivot surface to a distal tip of the elongate extraction blade.

10. The orthopedic extraction instrument of claim 1 wherein the surface of the blade comprises a planar surface.

11. The orthopedic extraction instrument of claim 1 wherein the pivot surface extends away from the elongate extraction blade in a direction perpendicular to the longitudinal axis of the elongate shaft.

* * * * *